United States Patent
Ligthart et al.

(10) Patent No.: US 9,000,258 B2
(45) Date of Patent: Apr. 7, 2015

(54) ***XANTHOMONAS CAMPESTRIS* PV. *CAMPESTRIS* RESISTANT *BRASSICA* PLANT AND PREPARATION THEREOF**

(75) Inventors: Johannes Theodorus Wilhelmus Ligthart, Warmenhuizen (NL); Roelof Marinus Veenstra, Warmenhuizen (NL); Klaas Biersteker, Sint Pancras (NL); Jan De Geus, Oudkarspel (NL); Hendrikus Stephanus Maria Huits, Heerhugowaard (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 35 days.

(21) Appl. No.: 13/132,575

(22) PCT Filed: Feb. 5, 2010

(86) PCT No.: PCT/EP2010/051426
§ 371 (c)(1),
(2), (4) Date: Aug. 4, 2011

(87) PCT Pub. No.: WO2010/089374
PCT Pub. Date: Aug. 12, 2010

(65) Prior Publication Data
US 2011/0289634 A1    Nov. 24, 2011

(30) Foreign Application Priority Data
Feb. 6, 2009    (NL) .................................... 1036531

(51) Int. Cl.
*A01H 1/00* (2006.01)
*A01H 1/02* (2006.01)
*A01H 1/04* (2006.01)
*C12Q 1/68* (2006.01)
*A01H 5/10* (2006.01)

(52) U.S. Cl.
CPC .. *A01H 1/00* (2013.01); *A01H 1/04* (2013.01); *A01H 5/10* (2013.01); *C12Q 1/6895* (2013.01)

(58) Field of Classification Search
USPC ................................................. 800/267, 306
See application file for complete search history.

(56) References Cited

U.S. PATENT DOCUMENTS 8,445,752 B2 *    5/2013    De Geus et al. .............. 800/306

OTHER PUBLICATIONS

Soengas et al (Theor Appl Genet 114: 637-645, 2007).*
Camargo et al (Phytopathology 85(10): 1296-1300, 1995).*
Ren et al (J Amer Soc Hort Sci 120(3): 548-555, 1995).*
Camargo et al., "Mapping of Quantitative Trait Loci Controlling Resistance of *Brassica oleracea* to *Xanthomonas campestris* pv. *campestris* in the Field and Greenhouse," Phytopathology, 85(10):1296-1300 (1995).
Soengas et al., "Identification of quantitative trait loci for resistance to *Xanthomonas campestris* pv. *campestris* in *Brassica rapa*," Theor Appl Genet, 114(4):637-645 (2006).
Taylor et al., "Sources and Origin Resistance to *Xanthomonas campestris*pv. *campestris* in *Brassica* Genomes," Phytopathology, 92(1):105-111 (2002).
Vincente et al., "Inheritance of Race-Specific Resistance to *Xanthomonas campestris* pv. *camp estris* in *Brassica* Genomes," Phytopathology, 92(10):1134-1141 (2002).
International Search Report dated Jul. 9, 2010.

* cited by examiner

*Primary Examiner* — Medina A Ibrahim
(74) *Attorney, Agent, or Firm* — Edward J. Baba; Daniel Stoddard; Bozicevic, Field & Francis LLP

(57) ABSTRACT

The present invention relates to a *Xanthomonas campestris* pv. *campestris* (Xcc) resistant *Brassica* plant, and seeds, fruits and or plant parts thereof, and to methods for preparation thereof. Specifically, the present invention relates to a Xcc resistant *Brassica oleracea* plant, and seeds, fruits and/or plant parts thereof, and methods for preparation thereof. Further, the present invention relates to Quantitative Trait Loci (QTL's) providing the present Xcc resistance and molecular markers, specifically Random Amplified Microsatellite Polymorphism (RAMP) markers, for identifying the present QTL's.

10 Claims, 2 Drawing Sheets

Figure 1:
Figure 2:

SEQUENCE LISTING

```
<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Synthetic primer

<400> SEQUENCE: 1
ttagctctct ctctctc                                                    17

<210> SEQ ID NO 2
<211> LENGTH: 16
<212> TYPE: DNA
<213> ORGANISM: Artificial Sequence
<220> FEATURE:
<223> OTHER INFORMATION: Synthetic primer

<400> SEQUENCE: 2
ccagcacaca cacaca                                                     16

<210> SEQ ID NO 3
<211> LENGTH: 16
<212> TYPE: DNA
<213> ORGANISM: Artificial Sequence
<220> FEATURE:
<223> OTHER INFORMATION: Synthetic primer

<400> SEQUENCE: 3
agattctctc tctctc                                                     16

<210> SEQ ID NO 4
<211> LENGTH: 15
<212> TYPE: DNA
<213> ORGANISM: Artificial Sequence
<220> FEATURE:
<223> OTHER INFORMATION: Synthetic primer
```

```
<400> SEQUENCE: 4
caactctctc tctct                                                15

<210> SEQ ID NO 5
<211> LENGTH: 16
<212> TYPE: DNA
<213> ORGANISM: Artificial Sequence
<220> FEATURE:
<223> OTHER INFORMATION: Synthetic primer

<400> SEQUENCE: 5
ttgtagagag agagag                                               16

<210> SEQ ID NO 6
<211> LENGTH: 16
<212> TYPE: DNA
<213> ORGANISM: Artificial Sequence
<220> FEATURE:
<223> OTHER INFORMATION: Synthetic primer

<400> SEQUENCE: 6
tctcttcttc ttcttc                                               16

<210> SEQ ID NO 7
<211> LENGTH: 15
<212> TYPE: DNA
<213> ORGANISM: Artificial Sequence
<220> FEATURE:
<223> OTHER INFORMATION: Synthetic primer

<400> SEQUENCE: 7
caactctctc tctct                                                15

<210> SEQ ID NO 8
<211> LENGTH: 16
<212> TYPE: DNA
<213> ORGANISM: Artificial Sequence
<220> FEATURE:
<223> OTHER INFORMATION: Synthetic primer

<400> SEQUENCE: 8
gaaatctctc tctctc                                               16
```

XANTHOMONAS CAMPESTRIS PV. CAMPESTRIS RESISTANT BRASSICA PLANT AND PREPARATION THEREOF

The present invention relates to a *Xanthomonas campestris* pv. *campestris* (Xcc) resistant *Brassica* plant, and seeds, fruits and/or plant parts thereof, and to methods for preparation thereof. Specifically, the present invention relates to an Xcc resistant *Brassica oleracea* plant. The invention also relates to the seeds, fruits and/or other plant parts from these resistant plants. Further, the present invention relates to Quantitative Trait Loci (QTL's) providing the present Xcc resistance and molecular markers, specifically Random Amplified Microsatellite Polymorphism (RAMP) markers, for identifying the present QTL's.

The microorganism *Xanthomonas campestris* pv. *campestris* is the primary causative agent of blackrot in Cruciferae. Worldwide, the microorganism probably is the main pathogen for diseases of Cruciferae. Blackrot is commonly found in parts of Europe, America, Africa, Asia, Australia and Oceania. The main host plant for this bacterial disease is *Brassica oleracea*. However, blackrot is also found in other Cruciferae, weeds and ornamental plants.

Infection with *Xanthomonas campestris* pv. *campestris* generally occurs through hydathodes of the leaves or in some cases through stomata or injuries. Following primary infection, the microorganism spreads through the vascular bundles thereby causing black veins and V-shaped lesions in the leaves. As a consequence, a part, or parts, of the leaf withers and yellows.

*Xanthomonas campestris* pv. *campestris* is a seed transmissible disease capable of infecting plants from seeds in early stages of development. The microorganism is capable of surviving on seeds for a time period up to three years. Infection with the microorganism can also occur through plant part storage, secondary host plants and irrigation systems.

Control of the disease through chemical agents is not possible. The only measures available to combat the disease are the use of disease free, i.e., microorganism free, starting materials and sanitary measures such as removal of infected host plants. Disease free starting material can be obtained by the use of pathogen free seeds or by physically treating infected seeds. The use, and the availability, of resistant plant species, which also remain free from Xcc infection during the growth season, is strongly preferred in order to cultivate healthy plants, i.e. Xcc free plants.

*Brassica* is a plant genus of the family of Brassicaceae (formerly referred to as Cruciferae). The members of this genus are also known as cabbage or mustard. The genus *Brassica* comprises a number of important agricultural and horticultural crops, including rape, cauliflower, red cabbage, savoy cabbage, white cabbage, oxheart cabbage, curly cale cabbage, broccoli, Brussels sprouts, Chinese cabbage, turnip cabbage and Portuguese cabbage (*tronchuda*).

A variety of plant parts of *Brassica* plants is used for consumption such as roots (turnip), stalks (turnip cabbage), leaves (e.g. white and red cabbage), axillary buds (sprouts), flowers (cauliflower, broccoli). Further, rape and rape seed are also used for providing vegetable oils. Some species with white or purple flowers, or a distinct colour or shape of the leaves, are cultivated for ornamental purposes.

Considering the importance of *Brassica* plants for food production and the economic losses associated with *Xanthomonas campestris* pv. *campestris* infection, it is an object, amongst other objects, of the present invention to provide a Xcc resistant *Brassica* plant and methods for the preparation thereof.

The need for a Xcc resistant *Brassica* plant is further indicated by the absence of adequate, cost-effective, and efficient means for controlling blackrot. For instance, there is no biocide available against the bacterium.

The above objects of the present invention, amongst other objects, are met by a method for providing Xcc resistant *Brassica* plants as defined in the appended claim 1.

Specifically, above objects of the present invention, amongst other objects, are met by a method for providing a *Xanthomonas campestris* pv. *campestris* resistant *Brassica* acceptor plant comprising:

- selecting a first *Brassica oleracea* donor plant which comprises a Quantitative Trait Locus 1 (QTL1) in its genome;
- selecting a second *Brassica oleracea* donor plant which comprises a Quantitative Trait Locus 2 (QTL2) in its genome; and
- introgression of, or genomically combining, Quantitative Trait Locus 1 (QTL1) from the first donor plant and Quantitative Trait Locus 2 (QTL2) from the second donor plant in a *Brassica* acceptor plant;

wherein,

Quantitative Trait Locus 1 (QTL1) is characterized by one or more RAMP markers chosen from the group consisting of a fragment of 158 to 162 bp with primer combination SEQ ID No: 1 and primer 6; a fragment of 283 to 287 bp with primer combination SEQ ID No: 2 and primer 6; a fragment of 370 to 374 bp with primer combination SEQ ID No: 3 and primer 6; and a fragment of 41 to 45 bp with primer combination SEQ ID No: 4 and primer 6;

Quantitative Trait Locus 2 (QTL2) is characterized by one or more RAMP markers chosen from the group consisting of a fragment of 88 to 92 bp with primer combination SEQ ID No: 5 and primer 6; a fragment of 125 to 129 bp with primer combination SEQ ID No: 6 and primer 6; a fragment of 334 to 338 bp with primer combination SEQ ID No: 7 and primer 6; and a fragment of 47 to 51 bp with primer combination SEQ ID No: 8 and primer 6; and wherein the *Brassica* acceptor plant is, regarding its genome, not identical to the first and second *Brassica* donor plants.

According to this first aspect of the present invention, selecting, or identifying, of the first and second donor plant is provided by determining the presence of Quantitative Trait Loci (QTL's) relating to the present Xcc resistance in the genome of the respective donor plants.

Such determination can preferably be provided by using standard molecular biological techniques which are commonly known in the art. An example of these techniques comprises isolating genomic DNA of a potential donor plant followed by the determination of the presence of the relevant Quantitative Trait Loci (QTL) in the isolated genome by, for example, PCR, DNA fingerprinting or Southern blots.

A particularly preferred method for identifying the present loci in the genome of respective donor plants is a DNA fingerprinting technique designated in the art as Random Amplified Microsatellite Polymorphism, or RAMP. According to this technique, a PCR reaction, or nucleic acid amplification reaction, is performed on isolated genomic material of the donor plant by using the present primers (SEQ ID Nos: 1 to 8) and RAPD primers (Operon RAPD 10-mer kits A-01-BH-20).

Following the PCR reaction, the amplification products obtained can be separated by, for example, gel electrophoresis and their size in basepairs can be determined, for example, by using a molecular basepair ladder. The Quantitative Trait Loci 1 and 2 (QTL1 and QTL2) according to the present invention are at least characterized by the presence of a band with the indicated basepair size, besides a possible plurality of other bands with other sizes not indicative for the resistance.

After selecting suitable donor plants, the loci (QTL1 and QTL2) identified in the donor plants can be introduced, or genomically combined, in the genome of the acceptor plant desired. This can, for example, be provided using standard crosses, or introgressions, wherein the inheritance of the present QTL's is determined in the progeny, preferably through determining the presence of the markers as described above. A particularly preferred technique is repeated backcrossing preferably in combination with marker analysis.

According to the present invention, the *Brassica* acceptor plant is, with respect to its genome, not identical to the first and second *Brassica* donor plants. In the present context, this can readily be determined by means of establishing a different phenotype between the donor and the acceptor plants indicative for the genome of the donor and acceptor plants or through a general genomic analysis.

Accordingly, the term " . . . regarding its genome, not identical . . . " according to the present invention indicates one or more, not Xcc resistance related, phenotypic differences between the donor plants and the acceptor plants. In other words the present acceptor plants are generally regarded in the art as a different plant.

According to a preferred embodiment of the present invention, the first *Brassica* donor plant and the second *Brassica* donor plant are identical with respect to their genome. This means that selecting a first and a second donor plant comprises selecting one donor plant comprising both QTL1 as QTL2 in its genome. In other words, this preferred embodiment comprises identifying a suitable *Brassica* donor variety having both QTL1 and QTL2, followed by introducing QTL1 and QTL2 in the desired *Brassica* acceptor plant thereby providing Xcc resistance to this acceptor plant.

According to a preferred embodiment of the present invention, the Quantitative Trait Locus 1 (QTL1) is characterized by one or more RAMP markers chosen from the group consisting of a fragment of 160 bp with primer combination 1.1 (SEQ ID No: 1) and 6; a fragment of 285 bp with primer combination 1.2 (SEQ ID No: 2) and 6; a fragment of 372 bp with primer combination 1.3 (SEQ ID No: 3) and 6; and a fragment of 43 bp with primer combination 1.4 (SEQ ID No: 4) and 6.

According to another preferred embodiment of the present invention, the Quantitative Trait Locus 2 (QTL2) is characterized by one or more RAMP markers chosen from the group consisting of a fragment of 90 bp with primer combination 2.1 (SEQ ID No: 5) and 6; a fragment of 127 bp with primer combination 2.2 (SEQ ID No: 6) and 6; a fragment of 336 bp with primer combination 2.3 (SEQ ID No: 7) and 6; and a fragment of 49 bp with primer combination 2.4 (SEQ ID No: 8) and 6.

According to a particularly preferred embodiment of the present invention, selecting of donor plants comprises determining, or identifying, by means of molecular biological techniques, the presence of 1 or more, preferably 2 or more, more preferably 3 or more, and most preferably 4, of the present RAMP markers for the respective QTLs in the genome of the respective *Brassica* donor plants.

According to a most preferred embodiment of the present invention, selecting, or identifying, further comprises selecting homozygous Quantitative Trait Loci 1 and 2 (QTL's 1 and 2) in the first and second *Brassica* donor plant.

The *Brassica* acceptor plant according to the present invention is preferably a *Brassica oleracea* plant, preferably chosen from the group consisting of *Brassica oleracea* convar. *botrytis* var. *botrytis* (cauliflower, romanesco), *Brassica oleracea* convar. *botrytis* var. *cymosa* (broccoli), *Brassica oleracea* convar. *botrytis* var. *asparagoides* (sprouting broccoli), *Brassica oleracea* convar. *oleracea* var. *gemnifera* (Brussels sprouts), *Brassica oleracea* convar. *capitata* var. *alba* (white cabbage, oxheart cabbage), *Brassica oleracea* convar. *capitata* var. *rubra* (red cabbage), *Brassica oleracea* convar. *capitata* var. *sabauda* (savoy cabbage), *Brassica oleracea* convar. *acephela* var. *sabellica* (curly cale cabbage), *Brassica oleracea* convar. *acephela* var. *gongyloides* (turnip cabbage) and *Brassica oleracea* var. *tronchuda* syn. *costata* (Portuguese cabbage).

Considering the advantages of a Xcc resistant *Brassica* plant described above, the present invention relates, according to a further aspect, to a *Brassica* acceptor plant as defined above, and to seeds, fruits and/or other plant parts thereof, comprising in its genome a Quantitative Trait Locus 1 (QTL1) and a Quantitative Trait Locus 2 (QTL2) as defined above.

According to a particularly preferred embodiment of this aspect, the present invention relates to a *Brassica* plant with deposit number NCIMB 41553 as well as to the seeds, fruits and/or other plant parts thereof.

According to yet a further aspect, the present invention relates to the use of a Quantitative Trait Locus 1 (QTL1) and a Quantitative Trait Locus 2 (QTL2), as defined above, for providing a *Xanthomonas campestris* pv. *campestris* resistant *Brassica* acceptor plant.

According to yet a further aspect, the present invention relates to the use of one or more primers selected from the group consisting of SEQ ID Nos: 1 to 8 (primers 1.1, 1.2, 1.3, 1.4, 2.1, 2.2, 2.3, and 2.4, respectively) for providing a present *Xanthomonas campestris* pv. *campestris* resistant *Brassica* acceptor plant.

The present invention will be further exemplified using the following example of a preferred embodiment. This example is merely intended as illustrative, and not to limit the scope of the present invention as outlined in the appended claims by any means.

BRIEF DESCRIPTION OF THE DRAWINGS

FIG. 1 shows a field test wherein Xcc resistant and Xcc susceptible *Brassica*'s are present.

FIG. 2 shows the same image as FIG. 1 in full colour.

EXAMPLE

The breeding of *Xanthomonas campestris* pv. *campestris* (Xcc) resistance into *Brassica oleracea* is a complex process. Several varieties of Xcc are described and Xcc resistance is generally not observed in *Brassica oleracea*. The presently described resistances of *Brassica oleracea* to Xcc are of quantitative nature, i.e. the resistance, and the level thereof, is dependent on the genetic background. This implies that several genes are involved in this resistance, resulting in that degrees of resistance to Xcc may be observed.

In order to obtain a qualitative resistant *Brassica oleracea* plant, i.e., the resistance is observed independent of the genetic background, a genetic source is used in which the resistance is essentially recessive. Through a program of backcrossing, the resistance is introduced in various genetic backgrounds (susceptible parent lines). The resistance level of the plants is determined by a field test. Since the trait involved is recessive, each crossing with a susceptible plant is followed by an inbreed generation in order to obtain the trait in a homozygous form. The progeny of this generation must be tested for their resistance level in a field test. As a result, it will take at least two years for an annual and at least four years for a bi-annual plant, in order to visualize an effect of the new crossing.

Since the resistance involved can be expressed as different levels of resistance, the resistance is expressed in quantitative values (on a scale from 0 to 9, where 0 represents fully susceptibility and 9 represents completely resistance). It was shown that the resistance in the various genetic backgrounds showed a phenotypic gradation within a normal distribution, instead of a simple Mendelian inheritance. This distribution can shift towards susceptible implying that the inbreed generations, from crossings between the resistant source and various susceptible parent lines, provide different levels of resistant plants.

Based on the segregation ratios and the differences in resistance levels, it was demonstrated that the resistance level of the plant is determined by several genetic factors or Qualitative Traits Loci. In order to identify DNA markers indicative, or representative, of a quantitative trait, QTL analyses are often used. QTL's are independent chromosomal regions which, coupled to underlying genes, in combination explain, or indicate, a genetic trait.

Using DNA markers, a genome spanning QTL analysis was performed on *Brassica oleracea* populations with diverse genetic backgrounds. With plants of these diverse populations, field tests were performed in order to determine the resistance level of the individual plants. The data of the marker analysis and the scores of the field test enabled identification of QTL's responsible for the Xcc resistance observed.

In total, six independently inherited QTL's were identified contributing, in some degree, to the resistance level observed. The variation of resistance levels observed in the field between the plants is a result of the presence and/or absence of the QTL's and the various combinations thereof. Of the six QTL's identified, two QTL's, designated herein as QTL 1 and QTL 2, were present in each genetic background providing resistance. In other words, these two QTL's are indicative of a qualitative resistance while the other four remainder of the QTL's appear to contribute to quantitative resistance. One of these QTL's, i.e. QTL 1, can be considered as the major-QTL, i.e., the QTL providing the strongest contribution to the resistance observed.

Each *Xanthomonas campestris* pv. *campestris* resistant inbreed line obtained by the breeding process possesses this major-QTL. The second QTL has, similar to the major-QTL, a contribution to the quantitative resistance level. However, this contribution is not as large as from the major-QTL, although it is also independent of the genetic background.

The remaining four QTL's are found in the different genetic backgrounds. These four QTL's may have a modifying role which results in variation of the resistance level. This is exemplified in table 1 below, where *Brassica oleracea* plants 1 to 6 are examples to illustrate these observations.

TABLE 1

Overview of the influence of the several QTL's on the resistance to Xcc.

| | QTL1 | QTL2 | QTL3 | QTL4 | QTL5 | QTL6 | Level of resistance |
|---|---|---|---|---|---|---|---|
| plant 1 | + | + | + | + | + | + | resistant |
| plant 2 | + | + | ± | ± | ± | ± | resistant |
| plant 3 | − | − | − | − | − | − | susceptible |
| plant 4 | − | + | + | + | + | + | susceptible |
| plant 5 | + | − | + | + | + | + | susceptible |
| plant 6 | − | − | + | + | + | + | susceptible |

Legend to this table:
+ present
± may be present, depending on the exact genetic background.
− absent The use of DNA markers associated with the two major QTL's, i.e. QTL 1 and QTL 2, provided the opportunity to select for plants being resistant to Xcc.

A disease test alone will not inherently provide plants having both QTL's in a homozygous form. The disease test may also result in plants with a high resistance level having one or more QTL's in a heterozygous form which inherently will not provide a stabile resistance.

Performing a disease test with more than thousand plants is only possible for a limited number of crossings. However, use of DNA markers offered the opportunity to analyse more populations consisting of one thousand plants in order to preselect desired plants.

Besides this, the selection using DNA markers also offered the opportunity to perform repeated backcrossing wherein the two major QTL's were maintained. This method gained one or two year per crossing generation which means acceleration in the breeding program of ten till twenty years. This quicker method provides an accelerated introduction of the novel Xcc resistance into hybrid varieties.

An additional complicating factor in the production of hybrid varieties is the required presence of the recessive resistance in both parents. Preferably, both parental lines, or donor plants, are homozygous for the two major QTL's. By using DNA markers, the identification of parents homozygous for the two major QTL's and, accordingly, suitable for producing a new resistant hybrid, can be performed in a relatively short period of time.

Seeds of such a hybrid are deposited at the NCIMB, Aberdeen, Scotland, AB21, 9YA, UK with deposit number NCIMB 41553.

The two major QTL's are both characterized by four DNA markers which characterize the presence thereof in the source. QTL1 is the major QTL, and QTL2 is the minor QTL.

The DNA markers were generated by the RAMP technique. The RAMP technique, wherein an iSSR and a RAPD-primer are combined, provides band patterns comprising one or more DNA fragments therein specifically co-segregating with the resistance. By mapping the RAMP-fragments and phenotype resistance scores, closely linked RAMP-markers were identified which identify the QTL (table 2). The genetic distance between the DNA markers within the QTL is represented by centimorgans (cM).

The general PCR conditions used for generating the DNA markers were as follows:

PCR Mix for RAMP Reaction:

Per Reaction

~0.2 ng/μl genomic plant DNA
75 mM Tris-HCL (pH 8.8)
20 mM $NH_4SO_4$
0.01% (v/v) Tween20
2.8 mM $MgCl_2$
0.25 mM dNTPs
0.15 μM forward primer
0.20 μM reverse primer
0.04 units/μl Red Hot® DNA Polymerase (ABgene, Epsom)

PCR Program RAPD35:

| | | cycles |
|---|---|---|
| step 1: | 2 min. 93° C. | 1 |
| step 2: | 30 sec. 93° C. | |
| step 3: | 30 sec. 35° C. | |
| step 4: | heating with 0.3°/sec to 72° C. | |
| step 5: | 1 min. 30 sec 72° C. | |

-continued

| | cycles |
|---|---|
| repeat steps 2-5 | 40 |
| step 6: 5 min 72° C. | 1 |

PAGE/Licor:

For analysis of the RAMP patterns use was made of a "Gene ReadIR 4200 DNA analyzers" (Licor Inc.). On the basis of an optimal concentration of 6.5% acryl amide, fragments can be separated which have a difference in size of a single base.

In order to visualize the fragments in this system, it is necessary to use labelled (IRDye labels) primers. For this purpose a one/third of the amount of forward primer was replaced by a labelled primer with identical sequence.

Marker Overview

In the research leading to the present invention, the primers as shown in table 3 were used for generating the DNA markers as shown in table 2.

TABLE 2

Overview of RAMP markers per QTL

| QTL | RAMP primer combination | Fragment size (bp) | Position in QTL (cM) |
|---|---|---|---|
| 1 | 1.1 + 6 | 160 | 10.1 |
| 1 | 1.2 + 6 | 285 | 18.5 |
| 1 | 1.3 + 6 | 372 | 20.9 |
| 1 | 1.4 + 6 | 43 | 21.3 |
| 2 | 2.1 + 6 | 90 | 28.5 |
| 2 | 2.2 + 6 | 127 | 29.4 |
| 2 | 2.3 + 6 | 336 | 36.3 |
| 2 | 2.4 + 6 | 49 | 37.2 |

TABLE 3

Overview of SEQ ID Nos

| SEQ ID No. | Primer | iSSR/RAPD | Sequence |
|---|---|---|---|
| 1 | 1.1 | iSSR | TTA GCT CTC TCT CTC TC |
| 2 | 1.2 | iSSR | CCA GCA CAC ACA CAC A |
| 3 | 1.3 | iSSR | AGA TTC TCT CTC TCT C |
| 4 | 1.4 | iSSR | CAA CTC TCT CTC TCT |
| 5 | 2.1 | iSSR | TTG TAG AGA GAG AGA G |
| 6 | 2.2 | iSSR | TCT CTT CTT CTT CTT C |
| 7 | 2.3 | iSSR | CAA CTC TCT CTC TCT |
| 8 | 2.4 | iSSR | GAA ATC TCT CTC TCT C |
| | 6 | RAPD | Operon RAPD ® 10-mer kits A-01 to BH20 (Operon Biotechnologies, Inc., Huntsville, USA |

The PCR reactions with the various primer combinations provide nucleic acid fragments with a basepair size indicated (see table 2) representative for the presence of the respective QTL. These DNA-markers are characteristic, or indicative, for the QTL's concerned. The combination of these DNA-markers, characterising the QTL, provides indisputable evidence of the presence of the QTL introgression from the Xcc resistant source in the donor plant.

DEFINITIONS cM—centimorgan—Unit for the genetic distance between markers, based on the number of crossovers per hundred individuals.

DNA marker—A DNA fragment which is linked to a gene or another DNA fragment with a known location on the genome, which is used to monitor the inheritance of this gene or this location.

Gel-electrophoresis—Method for separating molecules (DNA, RNA, proteins), on the basis of their size, shape or charge, in a matrix (agarose or polyacrylamide) under the influence of an electric field.

Inbred generation (self pollination)—Fertilization of an individual with its own pollen.

Introgression—A chromosome fragment of a line (cultivar) introduced, by way of crossing, into another line (cultivar).

IRDye labels—Infrared labels used for Licor imaging systems, the detection of which takes place at 700 nm or 800 nm.

Monogenic—Determined by a single gene.

PCR (Polymerase Chain Reaction)—An in vitro amplification method for multiplying a specific DNA fragment. This synthesis reaction makes use of a minimum of one oligonucleotide primer which hybridizes with a DNA fragment, after which a DNA polymerase amplifies the flanking region via successive temperature cycles.

Primer—A short oligonucleotide (~20-50 bp) complementary to the sequence of a single-strand DNA molecule, which serves as starting point of a polymerase.

QTL (Quantitative Trait Locus)—an independent chromosome region(s) which, when coupled to genes, together explain a trait.

RAMPs (Random Amplified Microsatellite Polymorphisms)—DNA fingerprinting technique based on RAPD and iSSR primers with which polymorphisms between different DNA samples are detected.

RAPD-primer (Random Amplified Polymorphic DNA primer)—A 10-mer with a "random" sequence, wherein the GC-content lies between 60% and 70% and wherein the primer ends are not self-complementary.

iSSR (inter Simple Sequence Repeat)—A primer designed on the 5' end of an SSR (Single Sequence Repeat); a DNA fragment consisting of repetitions of 2 or 3 nucleotides BC (Backcrossing)—Crossing of an individual with one of the original parents.

XCC Xanthomonas campestris pv. campestris.

| 0-1 | Form PCT/RO/134 (SAFE) Indications Relating to Deposited Microorganism(s) or Other Biological Material (PCT Rule 13bis) | |
|---|---|---|
| 0-1-1 | Prepared Using | PCT Online Filing Version 3.5.000.204 MT/FOP 20020701/0.20.5.9 |
| 0-2 | International Application No. | |
| 0-3 | Applicant's or agent's file reference | 4/2IM63/11 |
| 1 | The indications made below relate to the deposited microorganism(s) or other biological material referred to in the description on: | |
| 1-1 | page | 8 |
| 1-2 | line | 10* |
| 1-3 | Identification of deposit | |
| 1-3-1 | Name of depositary institution | NCIMB NCIMB Ltd. |

-continued

| | | |
|---|---|---|
| 1-3-2 | Address of depositary institution | Ferguson Building, Craibstone Estate, Bucksburn, Aberdeen AB21 9YA, United Kingdom |
| 1-3-3 | Date of deposit | 08 May 2008 (08 May 2008) |
| 1-3-4 | Accession Number | NCIMB 41553 |
| 1-5 | Designated States for Which Indications are Made | All designations |
| 2 | The indications made below relate to the deposited microorganism(s) or other biological material referred to in the description on: | |
| 2-1 | page | 13* |
| 2-2 | line | 1-3* |
| 2-3 | Identification of deposit | |
| 2-3-1 | Name of depositary institution | NCIMB NCIMB Ltd. |
| 2-3-2 | Address of depositary institution | Ferguson Building, Craibstone Estate, Bucksburn, Aberdeen AB21 9YA, United Kingdom |
| 2-3-3 | Date of deposit | 08 May 2008 (08 May 2008) |
| 2-3-4 | Accession Number | NCIMB 41553 |
| 2-5 | Designated States for Which Indications are Made | All designations |
| 3 | The indications made below relate to the deposited microorganism(s) or other biological material referred to in the description on: | |
| 3-1 | page | 24* |
| 3-2 | line | 23* |
| 3-3 | Identification of deposit | |
| 3-3-1 | Name of depositary institution | NCIMB NCIMB Ltd. |
| 3-3-2 | Address of depositary institution | Ferguson Building, Craibstone Estate, Bucksburn, Aberdeen AB21 9YA, United Kingdom |
| 3-3-3 | Date of deposit | 08 May 2008 (08 May 2008) |
| 3-3-4 | Accession Number | NCIMB 41553 |
| 3-5 | Designated States for Which Indications are Made | All designations |
| | FOR RECEIVING OFFICE USE ONLY | |
| 0-4 | This form was received with the international application: (yes or no) | Yes |
| 0-4-1 | Authorized officer | Marina Micheli |
| | FOR INTERNATIONAL BUREAU USE ONLY | |
| 0-5 | This form was received by the international Bureau on: | 01 Mar. 2010 (01 Mar. 2010) |
| 0-5-1 | Authorized officer | Nathalie Wagner |

*RO/EP

The invention claimed is:

1. A method for providing a *Xanthomonas campestris* pv. *campestris* resistant *Brassica* acceptor plant, the method comprising:
    providing a first *Brassica oleracea* donor plant comprising a Quantitative Trait Locus 1 (QTL1) and a Quantitative Trait Locus 2 (QTL2) in its genome, wherein said *Brassica oleracea* donor plant is a *Brassica* plant with deposit number NCIMB 41553; and
    introgressing of, or genomically combining, Quantitative Trait Locus 1 (QTL1) and Quantitative Trait Locus 2 (QTL2) from the donor plant in a *Brassica* acceptor plant;
    wherein Quantitative Trait Locus 1 (QTL1) comprises one or more RAMP markers chosen from the group consisting of a fragment of 158 to 162 bp with primer combination SEQ ID No: 1 and primer 6; a fragment of 283 to 287 bp with primer combination SEQ ID No: 2 and primer 6; a fragment of 370 to 374 bp with primer combination SEQ ID No: 3 and primer 6; and a fragment of 41 to 45 bp with primer combination SEQ ID No: 4 and primer 6; and
    wherein Quantitative Trait Locus 2 (QTL2) comprises one or more RAMP markers chosen from the group consisting of a fragment of 88 to 92 bp with primer combination SEQ ID No: 5 and primer 6; a fragment of 125 to 129 bp with primer combination SEQ ID No: 6 and primer 6; a fragment of 334 to 338 bp with primer combination SEQ ID No: 7 and primer 6; and a fragment of 47 to 51 bp with primer combination SEQ ID No: 8 and primer 6; and
    wherein the *Brassica* acceptor plant is, regarding its genome, not identical with the *Brassica oleracea* donor plant.

2. The method according to claim 1, wherein the Quantitative Trait Locus 1 (QTL1) comprises by one or more RAMP markers chosen from the group consisting of a fragment of 160 bp with primer combination SEQ ID No: 1 and primer 6; a fragment of 285 bp with primer combination SEQ ID No: 2 and primer 6; a fragment of 372 bp with primer combination SEQ ID No: 3 and primer 6; and a fragment of 43 bp with primer combination SEQ ID No: 4 and primer 6.

3. The method according to claim 1, wherein the Quantitative Trait Locus 2 (QTL2) comprises by one or more RAMP markers chosen from the group consisting of a fragment of 90 bp with primer combination SEQ ID No: 5 and primer 6; a fragment of 127 bp with primer combination SEQ ID No: 6 and primer 6; a fragment of 336 bp with primer combination SEQ ID No: 7 and primer 6; and a fragment of 49 bp with primer combination SEQ ID No: 8 and primer 6.

4. The method according to claim 1, wherein the selecting comprises determining the presence of one or more RAMP markers in the genome of the *Brassica oleracea* donor plant by molecular biological techniques.

5. The method according to claim 1, wherein Quantitative Trait Locus 1 (QTL1) and/or Quantitative Trait Locus 2 (QTL2) comprise two or more RAMP markers in the genome of the *Brassica oleracea* donor plant.

6. The method according to claim 1, wherein Quantitative Trait Locus 1 (QTL1) and/or Quantitative Trait Locus 2 (QTL2) comprise three or more RAMP markers in the genome of the *Brassica oleracea* donor plant.

7. The method according to claim 1, wherein Quantitative Trait Locus 1 (QTL1) and/or Quantitative Trait Locus 2 (QTL2) comprises four RAMP markers in the genome of the respective *Brassica oleracea* donor plant.

8. The method according to claim 1, wherein the selecting comprises selecting homozygous Quantitative Trait Loci 1 and 2 (QTL's 1 and 2) in the *Brassica oleracea* donor plant.

9. The method according to claim 1, wherein the *Brassica* acceptor plant is a *Brassica oleracea* plant.

10. The method according to claim 1, wherein the *Brassica* plant is chosen from the group consisting of *Brassica oleracea* convar. *botrytis* var. *botrytis* (cauliflower, romanesco), *Brassica oleracea* convar. *botrytis* var. *cymosa* (broccoli), *Brassica oleracea* convar. *botrytis* var. *asparagoides* (sprouting broccoli), *Brassica oleracea* convar. *oleracea* var. *gemnifera* (Brussels sprouts), *Brassica oleracea* convar. *capitata* var. *alba* (white cabbage, oxheart cabbage), *Brassica oleracea* convar. *capitata* var. *rubra* (red cabbage), *Brassica oleracea* convar. *capitata* var. *sabauda* (savoy cabbage), *Brassica oleracea* convar. *acephela* var. *sabellica* (curly cale cabbage), *Brassica oleracea* convar. *acephela* var. *gongyloides* (turnip cabbage) and *Brassica oleracea* var. *tronchuda* syn. *costata* (Portuguese cabbage).

* * * * *